United States Patent
Pfrang

(10) Patent No.: US 9,579,493 B2
(45) Date of Patent: Feb. 28, 2017

(54) DEVICE FOR APPLYING A NEEDLE ARRAY TO BIOLOGICAL TISSUE

(71) Applicant: Gerresheimer Regensburg GmbH, Regensburg (DE)

(72) Inventor: Juergen Pfrang, Kallmuenz (DE)

(73) Assignee: Gerresheimer Regensburg GMBH, Regensburg (DE)

( * ) Notice: Subject to any disclaimer, the term of this patent is extended or adjusted under 35 U.S.C. 154(b) by 0 days.

(21) Appl. No.: 14/574,361

(22) Filed: Dec. 17, 2014

(65) Prior Publication Data

US 2015/0165183 A1 Jun. 18, 2015

(30) Foreign Application Priority Data

Dec. 18, 2013 (DE) .................. 10 2013 021 058

(51) Int. Cl.
- *A61M 5/00* (2006.01)
- *A61M 37/00* (2006.01)
- *A61M 25/00* (2006.01)

(52) U.S. Cl.
CPC .. *A61M 37/0015* (2013.01); *A61M 2025/0092* (2013.01); *A61M 2037/003* (2013.01); *A61M 2037/0023* (2013.01); *A61M 2037/0046* (2013.01); *A61M 2037/0061* (2013.01)

(58) Field of Classification Search
CPC .............. A61M 5/158; A61M 37/0015; A61M 2005/1585; A61M 2037/0023; A61M 2037/0046; A61M 2005/14252
USPC .................. 604/173, 46, 47, 20, 22, 93.01
See application file for complete search history.

(56) References Cited

U.S. PATENT DOCUMENTS

| | | | |
|---|---|---|---|
| 6,332,875 B2 * | 12/2001 | Inkpen | ................ 604/117 |
| 7,097,631 B2 * | 8/2006 | Trautman | ............ A61B 17/205 |
| | | | 604/22 |
| 2003/0208167 A1 | 11/2003 | Prausnitz et al. | |
| 2012/0010529 A1 | 1/2012 | Chickering, III et al. | |
| 2012/0029434 A1 | 2/2012 | Kobayashi et al. | |

FOREIGN PATENT DOCUMENTS

| | | |
|---|---|---|
| WO | 01/93931 | 12/2001 |
| WO | 03/074102 | 9/2003 |

OTHER PUBLICATIONS

German First Office Action, dated Aug. 5, 2014, in European Patent Application No. 10 2013 021 058.5, priority application, 6 pp.

* cited by examiner

*Primary Examiner* — Phillip Gray
(74) *Attorney, Agent, or Firm* — Lathrop & Gage LLP

(57) ABSTRACT

The invention relates to a device for applying a needle array (1) to biological tissue (2), comprising a needle array holder (6) carrying the needle array (1), a pre-tensioning geometry (3) and an actuating element (4), wherein the actuating element (4) is so configured that, during its actuation, in a first step it transfers the pre-tensioning geometry (3) into a pre-tensioning position on the biological tissue (2) while pre-tensioning the biological tissue, and in a second step it transfers the needle array (1) into an application position on the biological tissue (2), while in this respect the pre-tensioning geometry (3) is held in the pre-tensioning position by the actuating element (4).

17 Claims, 7 Drawing Sheets

DEVICE FOR APPLYING A NEEDLE ARRAY TO BIOLOGICAL TISSUE

CROSS-REFERENCE TO RELATED APPLICATIONS

This application is a U.S. Nonprovisional Application filed under 35 U.S.C. §111(a) which claims the benefit of German Application No. 10 2013 021 058.5, filed Dec. 18, 2013. This application is hereby incorporated by reference in its entirety.

BACKGROUND OF THE INVENTION

This invention relates to a device for applying a needle array to biological tissue.

Needle arrays are often used to administer pharmaceuticals in a manner that is as pain-free as possible for the patient. In this respect, a plurality of individual needles is arranged on the needle array. The needles can be in solid or hollow form. However, in this respect a problem is that, as a needle array penetrates the skin, the so-called "bed of nails" effect occurs. In this respect the skin at the outer needles is stretched, but it rests on the inner needles almost as if on a solid body. As a result, the inner needle tips may not reliably penetrate the skin and administer the pharmaceutical as desired.

It has therefore already been proposed to pre-tension the skin by means of a tensioning geometry before the pharmaceutical is administered by a needle array. Such devices are described, for example, in WO2003/074102 A2 and WO2001/93931 A1.

In the devices therein, the skin is pre-tensioned by means of a pre-tensioning geometry so that the needles of the needle array are better able to penetrate into the skin. However, in this respect it has been found that the application is not uniformly reproducible. The depth of penetration in this respect is in turn dependent on the force with which the person who places the needle array on the skin presses against the application surface on the skin.

Accordingly, the object of the invention is to further develop a device for applying a needle array to biological tissue in such a manner that application of the needle array to biological material can take place reproducibly with in each case the same force, so that it is ensured that substantially all the needles of the needle array reach the desired depth of penetration into the biological tissue without, however, exceeding it.

This object is achieved by a device for applying a needle array to biological tissue having features as described herein. Advantageous embodiments of the invention will be found as described in the claims.

SUMMARY OF THE INVENTION

The device according to the present invention for applying a needle array to biological tissue has to that end a needle array holder carrying the needle array, a pre-tensioning geometry and an actuating element. In this respect the actuating element is so configured that, during its actuation, in a first step it transfers the pre-tensioning geometry into a pre-tensioning position on the biological tissue while pre-tensioning the biological tissue, and in a second step it transfers the needle array into an application position on the biological tissue, while in this respect the pre-tensioning geometry is held in the pre-tensioning position.

As a result of the configuration according to the invention of the device it is then possible for the needle array holder not to be pressed directly onto the biological tissue but to be applied to the biological tissue by means of an actuating element. In order that the depth of penetration is reached, where possible, for all the needles of the needle array, the pre-tensioning geometry is in a first step transferred to the biological tissue by the actuating element. The biological tissue is thereby pre-tensioned in an arc shape so that, on subsequent application of the needle array, while the pre-tensioning geometry is held in its pre-tensioning position, the needles on the inside of the needle array first come into contact with the biological tissue that is to be penetrated. Upon further actuation of the actuating element, the outer needles of the needle array are subsequently pressed onto the biological tissue, the tissue pre-tensioned in an arc shape being flattened again by the force applied by the needle array. As a result of this configuration according to the invention of the device, the "bed of nails" effect described at the beginning is reliably prevented from occurring. In addition, the device according to the invention ensures that application of the needle array to the biological tissue takes place with the same force on each application, because the pre-tensioning geometry first pre-tensions the biological tissue that is to be penetrated in the same manner on each application and then, as the actuating element is actuated further, the needle array is applied in each case with the same force to the biological tissue that is to be penetrated.

According to a first advantageous concept of the invention, in this respect the device is substantially in the form of a hollow cylindrical housing which has at one end an opening for application of the needle array. In this respect, in the housing, the pre-tensioning geometry, the needle array holder and the actuating element are held preferably displaceably, in particular acted upon by spring force by means of springs. As a result of this embodiment of the invention, it is possible for the device to be of very compact construction so that it is simple and reliable to use.

It has been found to be advantageous for the pre-tensioning geometry also to be in substantially hollow cylindrical form, the needle array holder being held displaceably therein, preferably in the form of a pin. In that respect, the entire device can be produced substantially in pin form, for example as an application pen.

According to a further concept of the invention, in this respect the actuating element projects out of the housing in its starting position and, for carrying out the application of the needle array, can be displaced into the housing through an opening in the housing. This embodiment of the invention makes it possible to provide a simple actuating mechanism for applying the needle array in such a device in the form of an application pen, which permits application of the needle array to the biological tissue in a reproducible manner, in particular with the same applied force.

In order to carry out the application of the needle array in a simple manner, mutually corresponding surfaces are provided on the actuating element, the pre-tensioning geometry and the needle array holder, which surfaces permit two-stage displacement of the pre-tensioning geometry and of the needle array holder. Advantageously, the mutually corresponding surfaces are in the form of sloping surfaces which slide on one another when the actuating element is displaced into the housing. During actuation of the actuating element, in this respect a sloping surface arranged on the actuating element slides on a corresponding sloping surface of the pre-tensioning geometry so that, upon further actuation of the actuating element, the pre-tensioning geometry is transferred from its starting position into its pre-tensioning position. If it has reached its pre-tensioning position, it is held in said pre-tensioning position by the sliding of corresponding surfaces of the actuating element and of the pre-tensioning geometry, while now, corresponding surfaces in the form of sloping surfaces of the actuating element and of the needle array holder slide on one another, the needle array holder being transferred from its starting position into the application position. The needle array holder thereby emerges from the opening at the end of the housing and from the pre-tensioning geometry, so that the needles of the needle array are able to penetrate into the biological tissue.

In order that simple handling and displacement of the actuating element, the pre-tensioning geometry and the needle array holder back into their starting position can be effected in a simple manner, springs are arranged between the individual elements. In this respect a spring, in particular a spiral spring, is arranged in each case between a support element of the actuating element and a support element of the housing and also between a further support element of the housing and a support element of the pre-tensioning geometry. Furthermore, a spring is arranged between a support element of the needle array holder and a support element of the pre-tensioning geometry, and a further spring is arranged between a support element of the housing and a further support element of the pre-tensioning geometry, these springs preferably also being in the form of spiral springs.

According to another concept of the invention, in this respect, the actuating element is in the form of a button which is displaceably arranged in an opening of the housing. Alternatively, the actuating element can also be in the form of a rotary button and can be provided with an external thread which cooperates with an internal thread of the opening of the housing. As a result of this configuration too, the actuating element is displaceable inside the opening of the housing so that it is able to displace both the pre-tensioning geometry and the needle array holder inside the housing.

It has further been found to be advantageous for a projection to be arranged on the needle array holder, which projection cooperates with a projection arranged on the pre-tensioning geometry in such a manner that displacement of the needle array from the pre-tensioning geometry beyond a predetermined depth of penetration of the needle array is avoided.

According to a further concept of the invention, the needles of the needle array are in the form of microneedles. Such microneedles are particularly suitable for administering pharmaceuticals into the skin of a patient because, when they are inserted into the skin, their size and depth of penetration means that they encounter only a small number of nerve cells and therefore cause scarcely any pain to the patient, it being possible for pharmaceuticals such as, for example, vaccines to be administered intradermally. Such microneedles do not penetrate the derma completely so that, for this reason too, the patient generally does not experience any pain on application. Such microneedles for administration of a pharmaceutical can also be either solid or in the form of hollow needles.

Further aims, advantages, features and possible uses of the present invention will become apparent from the following description of embodiments with reference to the drawings. In this respect all features described and/or represented in the figures form the subject matter of the present invention on their own or in any expedient combination, regardless of whether they are included in the claims or dependent claims.

DETAILED DESCRIPTION

Figure 1:
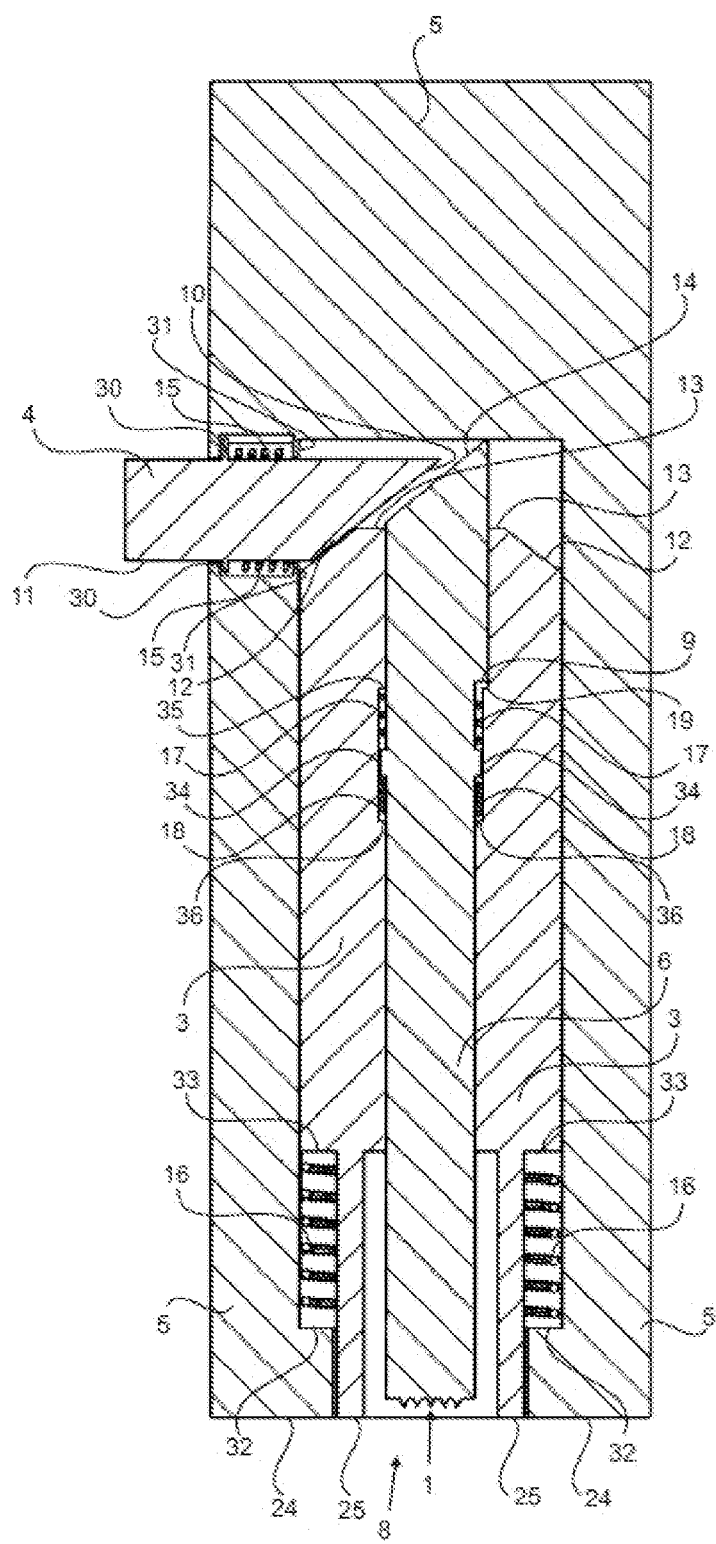
FIG. 1: is a cross-sectional view of a first embodiment of a device according to the invention in a starting position.

FIGS. 1 to 4 show an embodiment of a device according to the invention in different views and different positions. In this respect FIG. 1 shows, in a cross-sectional view, a starting position of the device according to the invention for applying a needle array 1 to biological tissue 2. In this respect the device is substantially in the form of a hollow cylindrical housing 5. A pre-tensioning geometry 3, which is likewise hollow cylindrical, is displaceably arranged in the housing 5 in such a manner that it is able to emerge from an opening 8 of the housing 5. Inside the hollow cylindrical pre-tensioning geometry 3 there is further arranged a needle array holder 6 which is held displaceably therein so that it can be displaced out of the pre-tensioning geometry 3 and the opening 8 of the housing 5. This embodiment further has an actuating element 4 in the form of a push button. The actuating element 4 is in this respect held captively but displaceably inside an opening 7 in the housing 5. In this respect, in the region of the opening 7 the housing 5 has a support element 31 on which a spring 15 is supported which is likewise supported on a support element 30 of the actuating element 4. By means of this spring 15, the actuating element 4, after actuation, can automatically be returned in a spring-loaded manner to its starting position according to FIG. 1. A spring 16 is likewise arranged between the pre-tensioning geometry 3 and the housing 5, which spring is supported on a support element 33 of the pre-tensioning geometry 3 and an element 32 of the housing. The spring 16 also serves automatically to return the pre-tensioning geometry into its starting position again after displacement thereof inside the housing 5.

Furthermore, two springs 17 and 18 are also arranged between the pre-tensioning geometry 3 and the needle array holder 6, the spring 17 being supported on a support element 35 of the pre-tensioning geometry and a support element 34 of the needle array holder, while the spring 18 is supported on a support element 34 of the needle array holder 6 and a support element 36 of the pre-tensioning geometry 3.

FIG. 1 shows the device in its starting state before administration of a pharmaceutical into a biological tissue 2 by means of the needle array 1. In this respect an edge 24 of the housing 5 and an edge 25 of the pre-tensioning geometry 3 are in alignment with one another in the region of the opening 8 of the housing 5. As a result, the device can reliably be positioned in a simple manner on a biological tissue 2 for administration of a pharmaceutical by means of the needle array 1.

Figure 2:
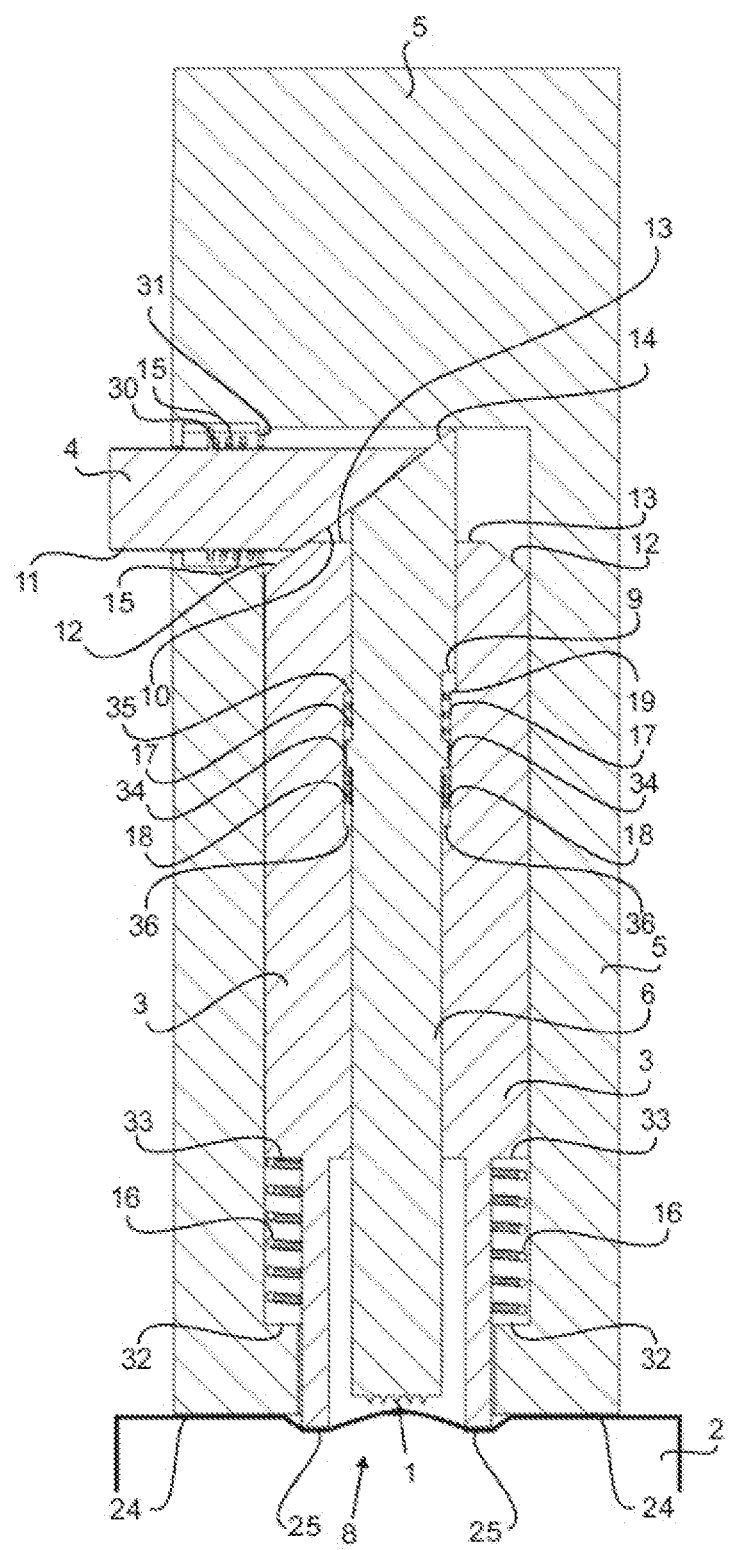
FIG. 2: is a cross-sectional view of the device of FIG. 1 during displacement of the actuating element.
Figure 3:
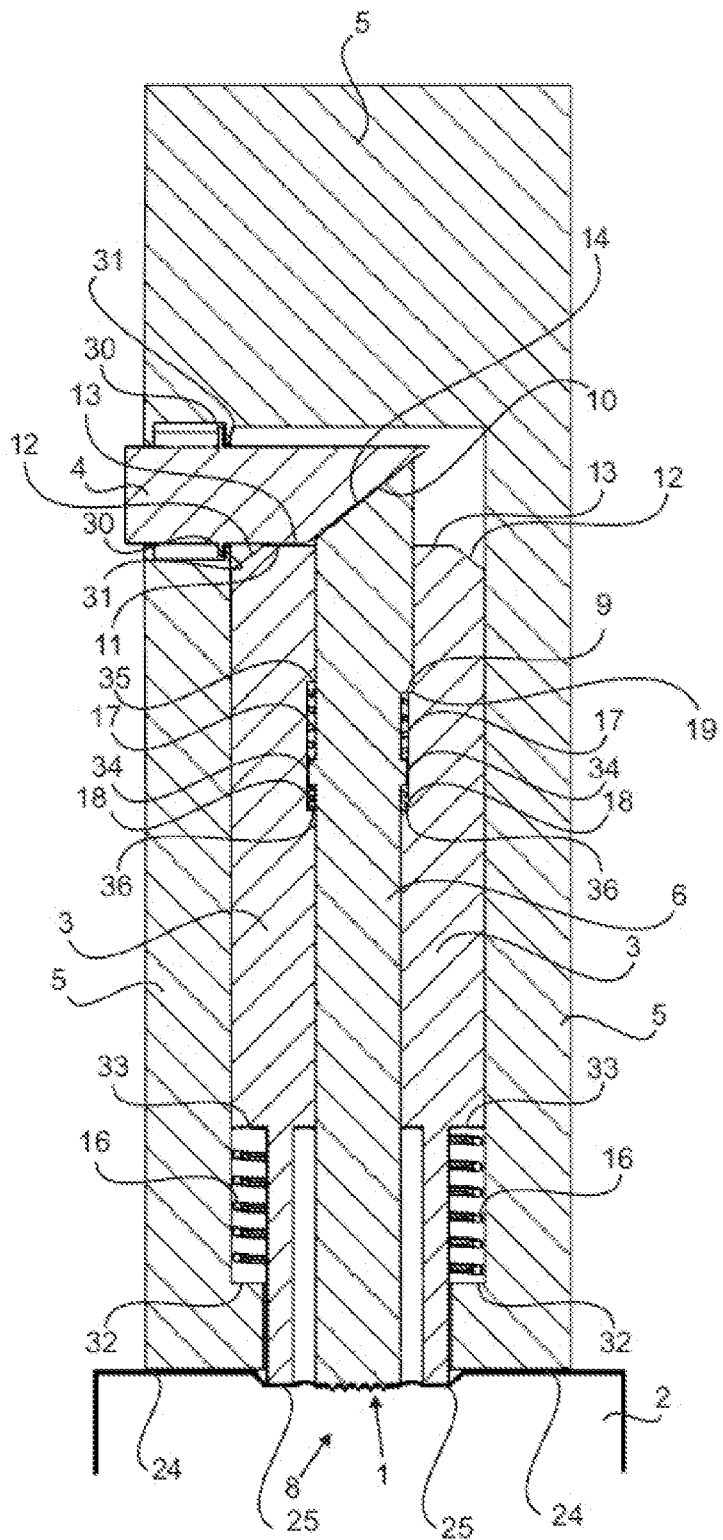
FIG. 3: is a cross-sectional view of the device according to FIGS. 1 and 2 with the actuating element in an end position.

FIG. 2 now shows the device of FIG. 1, wherein the device is already positioned with the edge 24 of the housing 5 on a biological tissue 2 and the actuating element 4 transfers the pre-tensioning geometry 3 from its starting position into its pre-tensioning position, which ultimately is reached only in the position shown in FIG. 3, however. During this transfer, a surface 10 in the form of a sloping surface of the actuating element 4 slides on a surface 12 in the form of a sloping surface of the pre-tensioning geometry and thereby displaces the pre-tensioning geometry 3 from its starting position according to FIG. 1 into the pre-tensioning position according to FIG. 3. In this pre-tensioning position, the housing 5 rests with the edge 24 on the biological tissue 2, while an edge 25 of the pre-tensioning geometry 3 has been pressed further into the biological tissue 2, the biological tissue being pre-tensioned in the shape of an arc.

If the actuating element 4 is then displaced further, the surface 10 in the form of a sloping surface of the actuating element 4 slides on a surface 14 in the form of a sloping surface of the needle array holder 6, the needle array holder then being displaced towards the biological tissue. In order that in this respect the pre-tensioning geometry 3 is not pressed further into the tissue 2, the surface 10 in the form of a sloping surface of the actuating element 4 no longer slides on the surface 12 in the form of a sloping surface of the pre-tensioning geometry 3. Instead, straight surfaces 11 and 13 of the actuating element 4 and of the pre-tensioning geometry 3 now slide on one another and thereby hold the pre-tensioning geometry 3 in its pre-tensioning position according to FIG. 3.

In FIG. 3, the needle array holder 6 is also shown with the maximum displacement, so that it has taken its application position in which the needles 1 penetrate into the tissue 2. In this respect a projection 9 is arranged on the needle array holder 6, which projection cooperates with a projection 19 of the pre-tensioning geometry 3 in such a manner that displacement of the needle array holder 6 beyond a predetermined depth of penetration of the needles of the needle array 1 into the biological tissue 2 is prevented. In this respect the projection 9 is supported on the projection 19, so that it cannot be displaced further without taking the pre-tensioning geometry 3 with it. In addition, further displacement of the needle array holder 6 is also no longer possible as a result of the maximum displacement of the actuating element 4 being reached.

Figure 5:
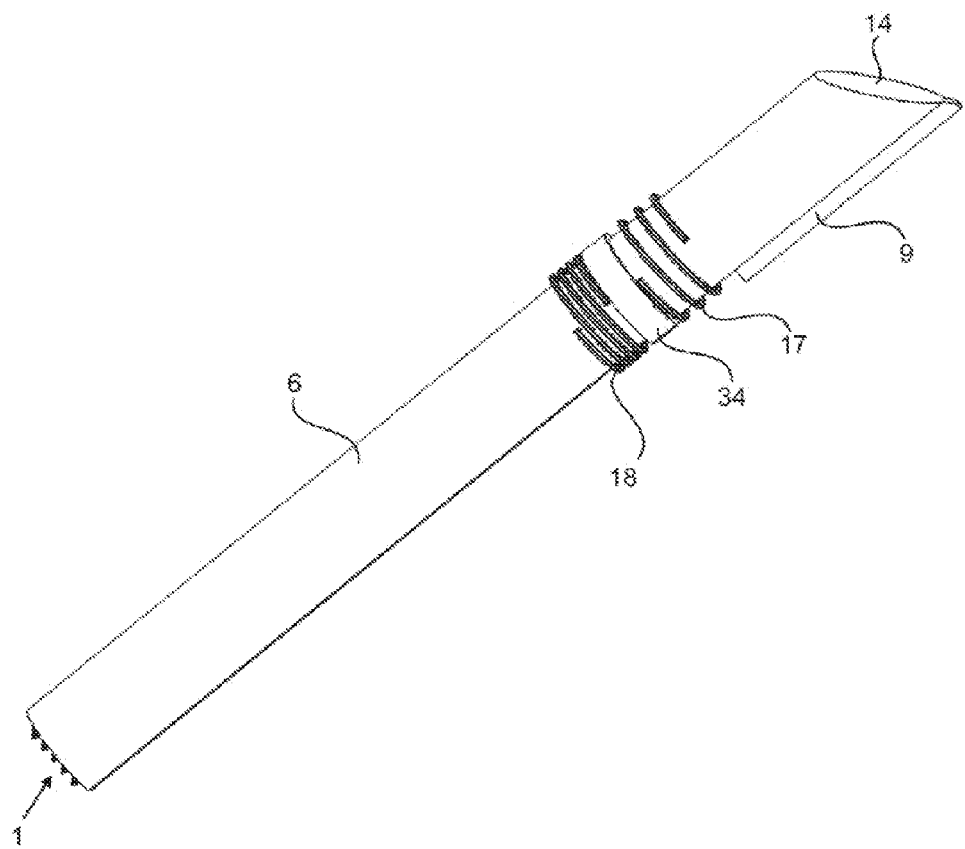
FIG. 5: is a perspective detailed view of the needle array holder of the device according to FIGS. 1 to 4.
Figure 7:
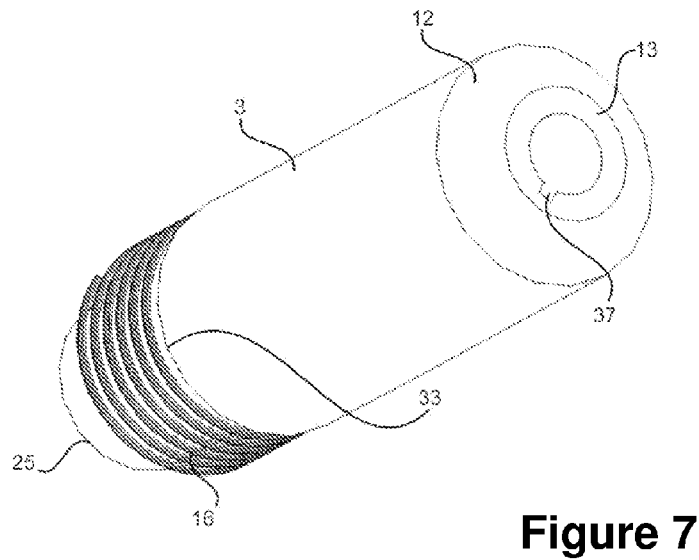
FIG. 7: is a detailed view of the pre-tensioning geometry of the device according to FIGS. 1 to 4.

As is apparent in particular from the detailed views of FIGS. 5 and 7, the projection 9 of the needle array holder 6 is guided in a guide 37 of the pre-tensioning geometry 3, the end of which forms the projection 19 of the pre-tensioning geometry.

Figure 4:
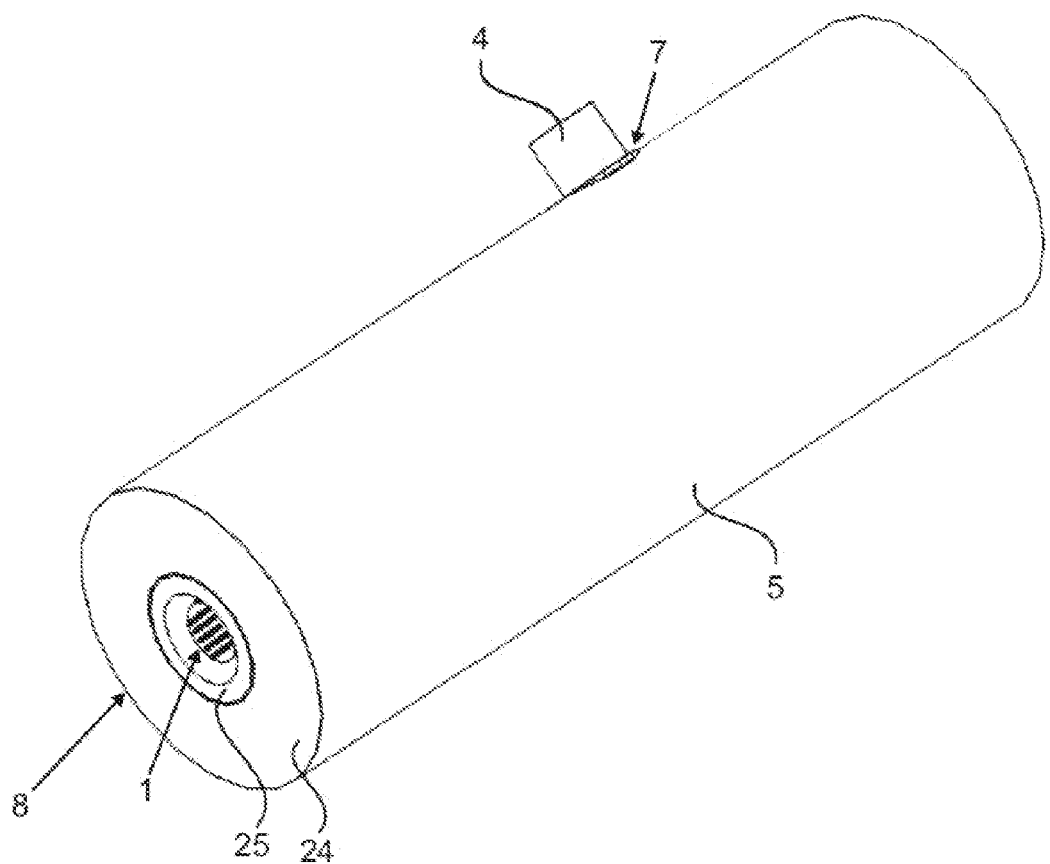
FIG. 4: is a perspective view of the device of FIG. 1.

FIG. 4 shows the device according to the invention of FIGS. 1 to 3, again in a perspective view. In this view, the opening 7 in which the actuating element 4 is displaceably held, the opening 8 and the edge 24 of the housing 5 can be seen in particular, the pre-tensioning geometry 3 with its edge 25 and the needle array 1 guided displaceably in the pre-tensioning geometry 3 by means of the needle array holder 6 also being visible in the opening 8.

Figure 6:
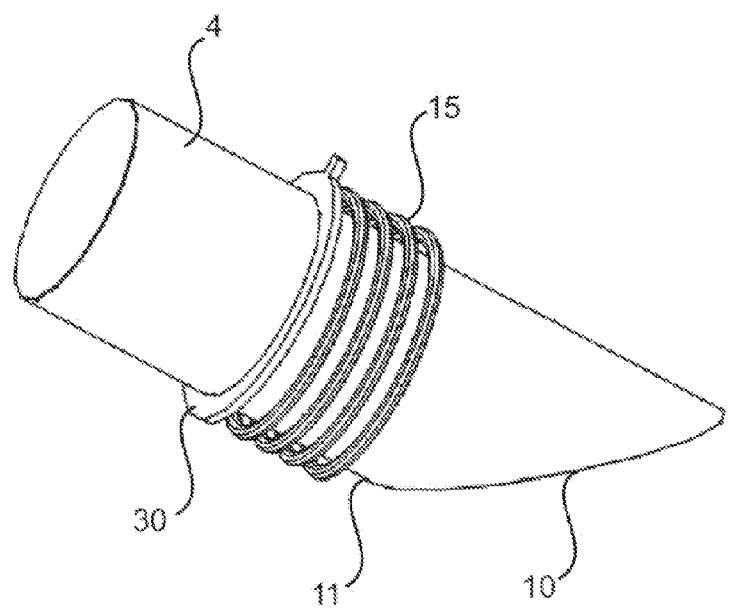
FIG. 6: is a perspective detailed view of the actuating element of the device of FIGS. 1 to 4.

In the detailed views of FIGS. 5 to 7 there can be seen in particular the springs 15, 16, 17 and 18 with the corresponding support elements 30, 33 and 34 of the actuating element 4, of the needle array holder 6 and of the pre-tensioning geometry 3.

The surfaces 10, 12 and 14 in the form of sloping surfaces, which slide on one another on actuation of the actuating element 4, can also be seen particularly clearly in these detailed views. Furthermore, the surface 13 of the pre-tensioning geometry 3 and the surface 11 of the actuating element 4 can be seen, which surfaces ensure that the pre-tensioning geometry 3 is held in its pre-tensioning position upon further displacement of the actuating element 4 and thus of the needle array holder 6.

Figure 8:
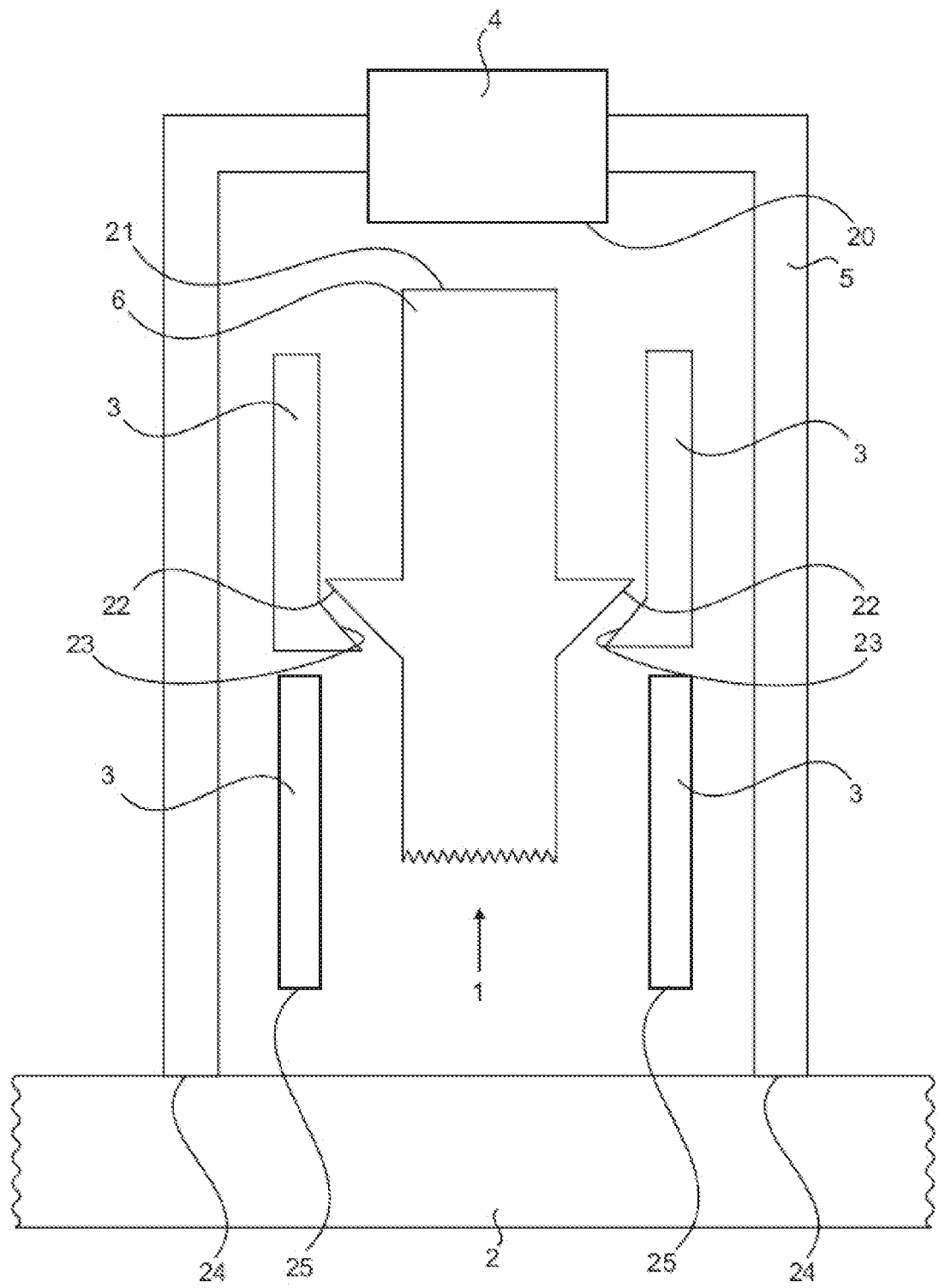
FIG. 8: is a cross-sectional view of a second embodiment of a device according to the invention.

Finally, FIG. 8 shows a second embodiment of a device according to the invention. The actuating element 4 is thereby in the form of a push button which, when actuated, presses with a surface 20 onto a surface 21 of the needle array holder 6.

As can be seen in FIG. 8, the housing 5 rests with an edge 24 on a biological tissue 2. If the actuating element 4 is then moved further, the pre-tensioning geometry 3 is also moved towards the biological tissue 2 by the needle array holder 6. As soon as the pre-tensioning geometry 3 is seated with an edge 25 on the tissue 2, the biological tissue 2 is pre-tensioned. This pre-tensioning continues until surfaces 22 in the form of sloping surfaces of the needle array holder 6 slide on one another on corresponding surfaces 23 in the form of sloping surfaces of the pre-tensioning geometry 3. As soon as those surfaces 22 and 23 no longer slide on one another and come out of engagement, the pre-tensioning geometry 3 is held in a pre-tensioning position by means which are not shown in this figure, and the needle array holder 6 is displaced further towards the biological tissue 2. Because the biological tissue 2 is pre-tensioned, it is ensured in the case of this device too, during application of the needle array 1, that all the needles of the needle array 1 reliably reach their required depth of penetration and the pharmaceutical is thus reliably administered into the biological tissue 2. Transfer of the needle array holder 6 and of the pre-tensioning geometry 3 can also be carried out automatically by means of springs, which are not shown here.

LIST OF REFERENCE NUMERALS

1 Needle array
2 Tissue
3 Pre-tensioning geometry
4 Actuating element
5 Housing
6 Needle array holder
7 Opening
8 Opening
9 Projection
10 Surface
11 Surface
12 Surface
13 Surface
14 Surface
15 Spring
16 Spring
17 Spring
18 Spring
19 Projection
20 Surface
21 Surface
22 Surface
23 Surface 24 Edge
25 Edge
30 Support element
31 Support element
32 Support element
33 Support element
34 Support element
35 Support element
36 Support element
37 Guide

The invention claimed is:

1. A device for applying a needle array to biological tissue, comprising a housing holding a needle array holder carrying the needle array, a pre-tensioning geometry, which is displaceably arranged in the housing, and an actuating element,
wherein in a starting position an edge, which determines an opening of the housing, is able to be positioned on the biological tissue, wherein the actuating element is so configured that, during actuation, in a first step the actuating element displaces the pre-tensioning geometry to emerge from said opening and thereby transfers the pre-tensioning geometry from the starting position into a pre-tensioning position on the biological tissue while pre-tensioning the biological tissue, and in a second step the actuating element transfers the needle array into an application position on the biological tissue, while in this respect the pre-tensioning geometry is held in the pre-tensioning position.

2. The device according to claim 1, wherein the housing comprises an opening for application of the needle array.

3. The device according to claim 2, wherein the needle array holder is held displaceably in the pre-tensioning geometry.

4. The device according to claim 2, wherein the actuating element projects from the housing in a starting position and can be displaced into the housing through the opening in the housing in order to carry out the application of the needle array.

5. The device according to claim 2, wherein mutually corresponding surfaces are provided on the actuating element, the pre-tensioning geometry and the needle array holder, wherein said surfaces permit two-stage displacement of the pre-tensioning geometry and of the needle array holder.

6. The device according to claim 5, wherein the mutually corresponding surfaces are in the form of sloping surfaces which slide on one another when the actuating element is displaced into the housing.

7. The device according to claim 2, wherein a first spring is arranged between a support element of the actuating element and a support element of the housing.

8. The device according to claim 7, wherein a second spring is arranged between a support element of the housing and a support element of the pre-tensioning geometry.

9. The device according to claim 7, wherein a third spring is arranged between a support element of the needle array holder and a support element of the pre-tensioning geometry, and a fourth spring is arranged between a support element of the needle array holder and a support element of the pre-tensioning geometry.

10. The device according to claim 2, wherein the actuating element is in the form of a push button or in the form of a rotary button which cooperates by means of an external thread with an internal thread of the opening of the housing.

11. The device according to claim 2, wherein a projection is arranged on the needle array holder, wherein said projection cooperates with a projection arranged on the pre-tensioning geometry in such a manner that displacement of the needle array from the pre-tensioning geometry beyond a predetermined depth of penetration is avoided.

12. The device according to claim 1, wherein the needles of the needle array are in the form of microneedles.

13. The device according to claim 2, wherein the housing is hollow cylindrical.

14. The device according to claim 2, wherein the pre-tensioning geometry is hollow cylindrical.

15. The device according to claim 2, wherein the pre-tensioning geometry, the needle array holder and the actuating element are held in the housing in such a manner that they can be displaced by spring force by means of one or more springs.

16. The device according to claim 2, wherein the pre-tensioning geometry, the needle array holder and the actuating element are held in the housing in such a manner that they can be acted upon by spring force by means of one or more springs.

17. The device according to claim 2, wherein the needle array holder is in the form of a pin.

* * * * *